(12) United States Patent
Nishiguchi et al.

(10) Patent No.: US 8,709,744 B2
(45) Date of Patent: Apr. 29, 2014

(54) MANUFACTURING PROCESS FOR CELLULAR SCREENING SUBSTRATUM, RESULTANT SUBSTRATUM, AND METHOD AND APPARATUS FOR SCREENING

(75) Inventors: Kenji Nishiguchi, Kanagawa (JP); Takeshi Miyazaki, Kanagawa (JP); Ryoichi Matsuda, Tokyo (JP); Kohei Watanabe, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 100 days.

(21) Appl. No.: 13/037,278

(22) Filed: Feb. 28, 2011

(65) Prior Publication Data

US 2011/0152123 A1   Jun. 23, 2011

Related U.S. Application Data

(62) Division of application No. 10/108,471, filed on Mar. 29, 2002, now abandoned.

(30) Foreign Application Priority Data

Mar. 29, 2001  (JP) ................................. 2001-097218

(51) Int. Cl.
| | |
|---|---|
| *C12Q 1/02* | (2006.01) |
| *C12N 11/00* | (2006.01) |
| *C12N 11/08* | (2006.01) |
| *C12N 5/00* | (2006.01) |
| *C12N 5/07* | (2010.01) |

(52) U.S. Cl.
USPC ............. 435/29; 435/174; 435/180; 435/395

(58) Field of Classification Search
None
See application file for complete search history.

(56) References Cited

U.S. PATENT DOCUMENTS

| | | | |
|---|---|---|---|
| 5,108,926 A | 4/1992 | Klebe | |
| 5,281,540 A | 1/1994 | Merkh et al. | |
| 6,083,763 A | 7/2000 | Balch | |
| 6,103,479 A | 8/2000 | Taylor | |
| 6,368,838 B1 | 4/2002 | Singhvi et al. | |
| 7,846,727 B2 | 12/2010 | Nishiguchi et al. | |

FOREIGN PATENT DOCUMENTS

| | | |
|---|---|---|
| WO | 97/45730 A1 | 12/1997 |
| WO | 00/39580 A1 | 7/2000 |

OTHER PUBLICATIONS

A. Lueking, et al., "Protein Microarrays for Gene Expression and Antibody Screening", Analytical Biochemistry, vol. 270, 1999, pp. 103 to 111.
B. Lemieux, et al., "Overview of DNA Chip Technology", Molecular Breeding, vol. 4, pp. 277 to 289, 1998.
A. Roda, et al., "Protein Microdeposition Using a Conventional Ink-Jet Printer", Biotechniques, vol. 28, 2000, pp. 492 to 496.
Avri Ben-Ze'ev, et al., "Protein Synthesis Requires Cell-Surface Contact while Nuclear Events Respond to Cell Shape in Anchorage-Dependent Fibroblasts", Cell, vol. 21, Sep. 1980, pp. 365-372.
Judah Folkman, et al., "Role of cell shape in growth control", Nature, vol. 273, Jun. 1, 1978, pp. 345-349.
D. Gospodarowicz, et al., "Determination of Cellular Shape by the Extracellular Matrix and Its Correlation with the Control of Cellular Growth", Cancer Research, vol. 38, Nov. 1978, pp. 4155-4171.
Donald E. Ingber, et al., "Endothelial Growth Factors and Extracellular Matrix Regulate DNA Synthesis Through Modulation of Cell and Nuclear Expansion", In Vitro Cellular & Developmental Biology, vol. 23, No. 5, May 1987, pp. 387-394.
Joos, et al., "A microarray enzyme-linked immunosorbent assay for autoimmune diagnostics", Electrophoresis, vol. 21, 2000, pp. 2641-2650.
Decision G 1/03, Enlarged Board of Appeal, Apr. 8, 2004.
Robert J. Klebe, Experimental Cell Research, vol. 179, 1988, pp. 362-373.
Protein, Nucleic Acid and Enzyme, vol. 45, No. 5, 2000, pp. 727-734.

*Primary Examiner* — David M Naff
(74) *Attorney, Agent, or Firm* — Fitzpatrick, Cella, Harper and Scinto

(57) ABSTRACT

The present invention provides cellular screening substrata which can be formed in simple processing steps. The cellular screening substrata can be formed which are characterized in that plural cellular screening substances are positioned and immobilized at predetermined positions on a base by microdroplet discharging means, and plural areas having different cellular screening functions are formed thereon.

24 Claims, 4 Drawing Sheets

MANUFACTURING PROCESS FOR CELLULAR SCREENING SUBSTRATUM, RESULTANT SUBSTRATUM, AND METHOD AND APPARATUS FOR SCREENING

This application is a divisional of application Ser. No. 10/108,471, filed Mar. 29, 2002, now abandoned, the contents of which are incorporated herein by reference.

BACKGROUND OF THE INVENTION

1. Field of the Invention

The present invention relates to cellular screening substrata capable of being used for identifying substances contributing to at least one of cell adhesion, proliferation, differentiation, survival, maintenance of undifferentiated state, and apoptosis, to their manufacturing processes, and to methods and apparatus for cellular screening using the cellular screening substrata.

2. Related Background Art

Recently, there have been actively carried out studies on culture of animal and plant cells under different conditions, or studies on products of particular cultured cells. Specifically, investigations have been made in various fields to produce, utilizing specific cellular activities, substances which are impossible to synthesize artificially or otherwise quite difficult to synthesize.

Also, there have been carried out studies to identify substances having an effect on cell proliferation and differentiation to proliferate or differentiate desired cells according to intended applications. With rapid progress in cell technology and medical engineering, attention has focused on microbiosensors or artificial organs using cells, and furthermore on neurocomputers and the like, and active research efforts have been made for these applications.

In order to utilize cells in vitro as stated above, however, it is indispensable to position cells as desired and to control their proliferation, differentiation, and production of substances. Mechanisms that control cell positioning, proliferation, differentiation, and production of substances, however, have not been sufficiently elucidated yet. Thus, it is quite difficult to culture cells controlling these cellular functions, which is one of the main obstacles to researches and developments utilizing cells as described above.

As an attempt to regulate the cell positioning, U.S. Pat. No. 5,108,926 discloses a method employing an ink jet printer to form a pattern of a cell adhesive protein on which cells are grown. By this method, cells can be cultured on the surface of the pattern where a cell adhesive protein was applied, but it is impossible to control their proliferation/differentiation and production of substances to screen the cells.

In an article (Proteins, Nucleic Acids and Enzymes, 45-5, 727-734 (2000), cell growth factors that effect proliferation and differentiation of cells were immobilized onto a support using a photolithography technique, and their effects on proliferation and differentiation of cells were studied. The substrate on which the cell growth factors had been immobilized, however, was not used as means for cellular screening. In addition, photolithographic procedures waste biological substances that exist only in small amounts in the body, and necessitate repeating the processes of exposure and development, complicating the production steps.

WO97/45730 proposes a method of screening cells by immobilizing a substance that influences cell adhesiveness onto a substrate. In this method, a reactive functional group provided on the substratum and a cell adhesive material is immobilized through a divalent crosslinking reagent. This method employs photolithography to bind the reactive functional group to the cell adhesive material. Thus, this method has problems as described above. In addition, when two or more cell adhesive materials are immobilized, it is almost impossible to avoid the binding of the material which has been already immobilized and a material to be newly immobilized at undesired locations through a divalent crosslinking reagent, and therefore it is very difficult to position cell adhesive materials on desired locations. Further, this method does not include immobilization of substances that affect cell proliferation, differentiation or production. In addition, according to this method, cells are fixed in wells through the cell adhesive materials, and screening is carried out by detecting substances produced by the cells during culture of the cells. Thus, this method is not a method for screening substances which have an effect on proliferation and differentiation, and furthermore production of substances, as in the present invention.

SUMMARY OF THE INVENTION

The present invention aims to provide a substratum for cellular screening that can solve the problems in the above-described prior arts, and can be prepared by simple procedures, and to provide a manufacturing process thereof, whereby providing basic techniques for further progress of researches in cell technology etc., and for manufacturing various devices utilizing cells.

Furthermore, the present invention aims to provide a method for screening substances which have an effect on at least one of cell adhesiveness, proliferation, differentiation, survival, maintenance of undifferentiated state, apoptosis, and production of substances, using cells cultured on such a substratum.

Results of screening allow identifying factor(s) necessary for cell proliferation or differentiation, survival, maintenance of undifferentiated state, apoptosis, or production of substances, and determining methods for efficient cell culture. In addition, if the substances to be immobilized are drugs, then it is possible to evaluate which combination of drugs and what amount exert the most effective effort on cultured cells. Alternatively, for example, by using a substratum on which sustained-release capsules of polyacrylamide gel etc. containing chemicals such as so-called endocrine disrupting chemicals are immobilized, and allowing gradual release of the chemicals from the capsules into the culture medium, it is possible to assess the sensitivity of human to such chemicals. Furthermore, based on the results of these assessments, it will be possible to determine a method of diagnosing individuals for various diseases.

According to one aspect, the present invention provides a cellular screening substratum, wherein plural cellular screening substances are positioned and immobilized at predetermined areas on a base by micro-droplet discharging means to form plural areas having different functions for cellular screening.

In an embodiment, the above-described areas at which screening substances have been immobilized may contain more than one area having a different combination of the immobilized cellular screening substances. In another embodiment, the plural areas at which screening substances have been immobilized may also contain more than one area having a different density of the immobilized cellular screening substances. In still another embodiment, each area or each area group of two or more areas may be formed within a sunken portion. Each area or each area group of two or more areas may be surrounded by a rising wall-shaped structure.

In another aspect, the present invention includes A process for manufacturing a cellular screening substratum, comprising the steps of positioning each of cellular screening substances at predetermined areas on a base by micro-droplet discharging means; and immobilizing the cellular screening substances at each area on the substratum.

In one embodiment, droplet-discharging means by a thermal ink jet method, or a piezoelectric ink jet method is used.

In one embodiment, external immobilizing energy is applied to immobilize a culture controlling substance on the base.

In still another aspect, the present invention provides a method for cellular screening using a cellular screening substratum according to claim 1, comprising the step of culturing cells in a culture medium in contact with the areas of the immobilized screening substances on the cellular screening substratum.

In one embodiment, t is possible to add one or more substances required for cellular screening to the culture medium in contact with the areas of the immobilized screening substances. It is also possible to carry out cell culture under conditions in which the areas of the immobilized screening substances are in contact with the flow of the culture medium, for example, by perfusing the culture medium.

Screening can be performed, based on the following. In this case, cells may be stained in advance.

1) Evaluation of morphological changes of cells in a desired area.
2) Quantitative measurement of a substance synthesized by the cells in a desired area on the substratum.
3) Quantitative measurement of a substance incorporated into the cells in a desired area on the substratum.
4) Quantitative measurement of a substance by determining the amount of radiation.
5) Quantitative measurement of a substance by determining the amount of fluorescence.
6) Quantitative measurement of a substance by determining the amount of light emission.
7) Quantitative measurement of a substance by determining the absorbance.

An apparatus for cellular screening using a cellular screening substratum as described above, wherein said apparatus comprises means for culturing the cells in a culture medium in contact with the areas of the immobilized screening substances on the cellular screening substratum.

DETAILED DESCRIPTION OF THE INVENTION

The present invention will be now described in detail below.

Figure 2:
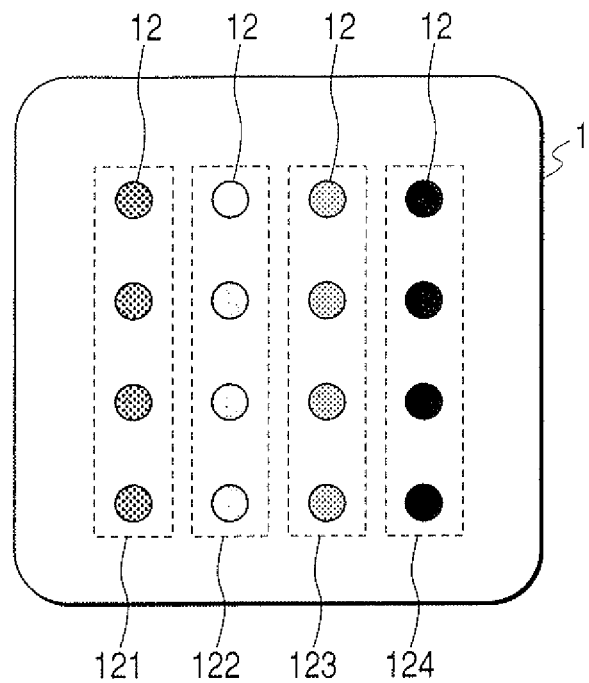
FIG. 2 is an example of positioning cellular screening substances on the cellular screening substratum of Example 1.

There will be explained one embodiment of the cellular screening substratum of the present invention. As shown in FIG. 2, the cellular screening substratum 1 has two or more (four in FIG. 2) substances to be screened with cells (hereinafter referred to as cellular screening substance or screening substance) 12 positioned on desired locations (121 to 124), each of the cellular screening substances 12 being immobilized on the base 11. Immobilization of two or more cellular screening substances 12 will make it possible to control at least one of adhesion, proliferation, and differentiation of cells to a high degree.

In the present invention, the cellular screening substances 12 refer to culture-controlling substances that effect cell adhesiveness onto a base 11, proliferation, differentiation, survival, maintenance of undifferentiated state, apoptosis, or production of substances, including extracellular matrix proteins, antibodies having an ability of binding specifically to the cell surface, cytokines, and other chemical substances.

Extracellular matrix proteins include, for example, collagen, elastin, fibronectin, laminin, and others. Cytokines include cell growth factors and hormones. Cell growth factors include nerve growth factors (NGFs), epidermal growth factors (EGFs), fibroblast growth factors (FGFs), and others. Hormones include insulin, adrenaline, and others.

Other chemical substances include substances such as allergens that cause allergy and various chemicals called endocrine disrupting chemicals. Immobilized cellular screening substances 12 form areas according to the difference in chemical or physical properties such as types of the cellular screening substances 12 and disposed patterns on the base 11.

The combination of cellular screening substances 12 can be different between areas or area groups of two or more areas on the base 11. This will allow observing the different effect of the combinations of substances 12 on at least one of cell adhesiveness, proliferation, differentiation, survival, maintenance of undifferentiated state, apoptosis, and production of substances.

The cellular screening substances 12 can be also represented at different densities according to the areas or area groups of two or more areas on the base 11. This will allow observing in more detail difference in cell adhesiveness, proliferation, differentiation, survival, maintenance of undifferentiated state, apoptosis, or production of substances due to differences in the density of cellular screening substances 12. Thus, one major advantage of employing droplet discharging means is that it is possible that cellular screening substances are readily positioned onto an immobilization area at a given ratio.

Immobilization of cellular screening substances 12 onto a base 11 can be made via a covalent bond, electrostatic attraction force, or biological affinity. When the cellular screening substances 12 are immobilized onto a base 11 by a covalent bond, the substances 12 can be immobilized with strong force, and the binding is hardly influenced depending on cells, culture medium, and the like, resulting in stable immobilization on the base 11.

Figure 1:
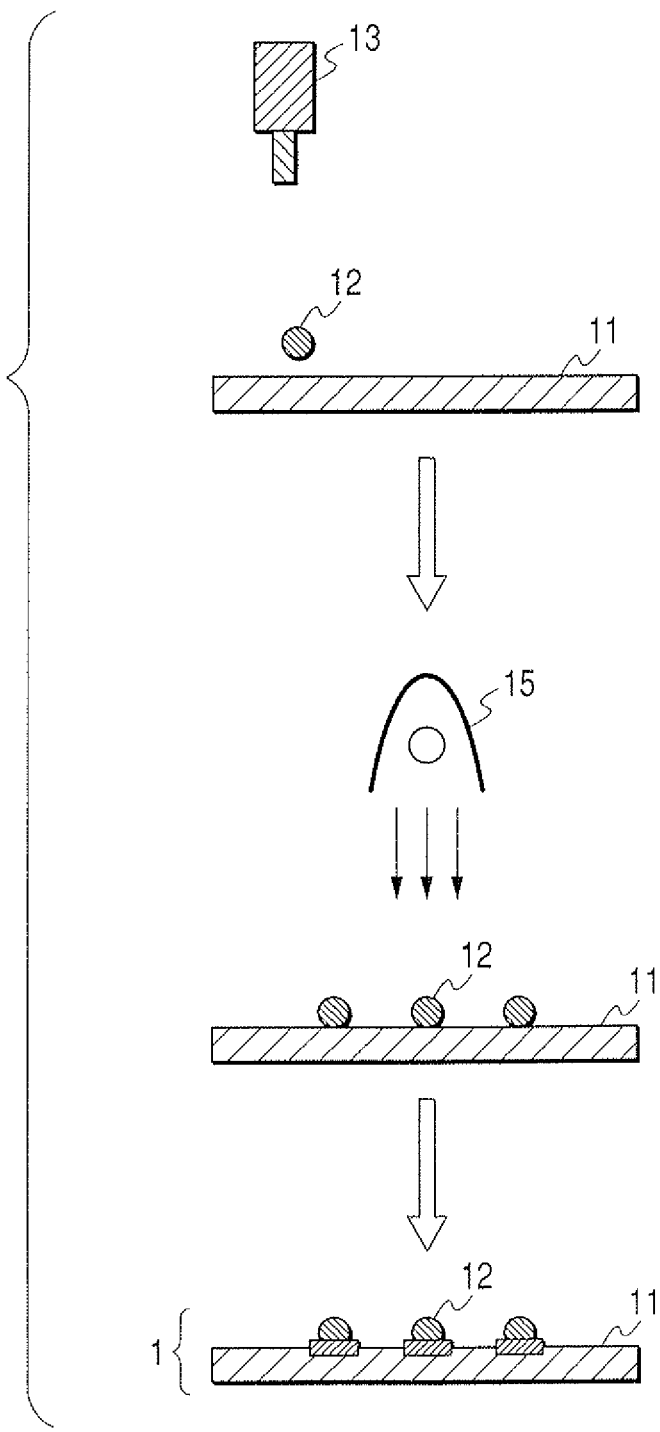
FIG. 1 is a schematic example of the process for manufacturing the cellular screening substratum of Example 1.

Now, referring to FIG. 1, an example procedure for immobilizing a substance 12 onto a base 11, in which insulin is employed as a substance 12 having an effect on at least one of cell adhesiveness, proliferation, differentiation, survival, maintenance of undifferentiated state, apoptosis, and production of substances.

First, 4-azidobenzoic acid N-hydroxysuccinimide ester is introduced into insulin as a linker (see the following scheme).

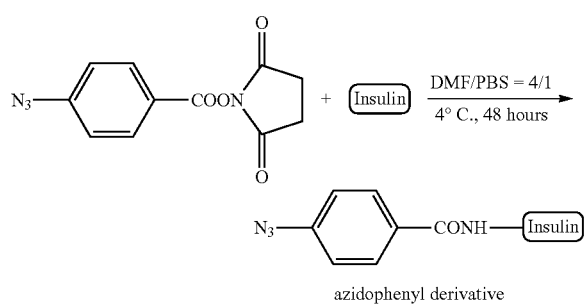

azidophenyl derivative

A solution of the linker-attached insulin 12 thus obtained is discharged, for example, onto a polyethylene terephthalate (PET) base 11, using liquid droplet discharging means 13 (an ink jet printer). Next, when this base is irradiated with light, for example, UV light, from a light source indicated by 15 in FIG. 1, and the azido group of the linker is cleaved to form an amide bond with a carbon atom on the PET base that the insulin 12 is covalently immobilized on the surface as shown in the following formula.

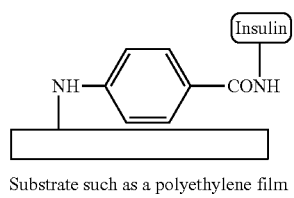

Substrate such as a polyethylene film

In the case of immobilization via electrostatic attraction force, the immobilization onto the base 11 can be achieved without chemical treatments, avoiding denaturation of cellular screening substances 12 due to chemical treatment. When biological affinity is utilized for immobilization onto a base 11, it is relatively easy to carry out treatments required for immobilizing cellular screening substances 12, and thus stable immobilization is achievable.

Base 11 can be of any material and of any shape, as long as the stable immobilization of cellular screening substances 12 can be obtained. Specifically, glass plates, plastic plates, plastic sheets, polymer films, papers, and the like can be suitably employed. Base 11 can be transparent, or light-shielding, or even colored. In order to immobilize cellular screening substances 12 onto a base 11, or in order to enhance the stability of cellular screening substances 12 on a base 11, portion or the entire of the surface of a base 11 can be treated with chemical (s), or by exposing it to radiation.

On a base 11, individual areas or area groups of two or more areas in which cellular screening substances 12 are immobilized may be sunken or depressed. This can facilitate the positioning of liquid droplets by micro-droplet discharging means, and in addition, permits cell culture changing the culture medium for every area or area group in the same sunken region. Bases having these depressions can made by die molding of resin materials, by etching procedures using photolithography techniques or by others.

On a base 11, individual areas or area groups of two or more areas in which cellular screening substances 12 are immobilized may be surrounded by a wall-shaped structure. This can facilitate the positioning of liquid droplets by micro-droplet discharging means, and in addition, permits the cell culture changing the culture medium in every area or every area group in the same depression. Such bases having wall-shaped microstructures can be made by employing photolithography methods etc.

A cellular screening substratum 1 of this type can be manufactured as follows (see FIG. 1). A base 11 may be optionally subjected to the above-described pretreatment first. Specifically, a base 11 can be subjected to various chemical and physical treatments such as washing to remove unwanted materials, radiation including UV light, or corona discharging. In addition, a polymer material or a silane coupling agent may be applied onto portion or the entire of the surface of a base 11, if necessary.

Cellular screening substances 12 are positioned on such a base 11. For positioning them is employed micro-droplet discharging mean 13. Here, micro-droplet discharging mean 13 refers to means capable of discharging liquid droplets having a volume of 100 pl or less per droplet, including micro-pipettes, micro-dispensers, discharging devices utilizing an ink jet method. In view of cost of the discharging device production and micro-droplet discharging ability, discharging devices utilizing an ink jet method can be suitably employed. Among ink jet methods, a thermal ink jet method and a piezoelectric ink jet method can be suitably employed. The discharging device of thermal ink jet method has advantages that micro-processing of the discharging port is easy, and it can dispose cellular screening substances 12 at high density. The discharging device of piezoelectric ink jet method generates discharging energy by the displacement of the piezoelectric element so that thermal stress is not applied to the cellular screening substances 12 and the substances 12 can be discharged without impairing their properties.

Cellular screening substances 12 can be dissolved in an appropriate solvent. Such a solvent may be any solvent, as long as it can dissolve cellular screening substances 12 without impairing their properties. Suitably used is water, preferably ion-exchanged (deionized) water, or otherwise various buffer solutions is preferable, because they dissolve cellular screening substances 12 without impairing their properties.

Aqueous solvents can be also used, if necessary. Aqueous solvents may be any solvent, as long as it dissolves in water, and include, for example, alkyl alcohols having up to 14 carbons, such as methyl alcohol, ethyl alcohol, n-propyl alcohol, isopropyl alcohol, n-butyl alcohol, sec-butyl alcohol, and ter-butyl alcohol; amides such as dimethylformamide and dimethylacetamide; ketones and keto alcohols such as acetone and diacetone alcohol; ethers such as tetrahydrofuran and dioxane; polyalkylene glycols such as polyethylene glycols and polypropylene glycols; alkylene glycols having an alkylene group containing 2 to 6 carbon atoms, such as ethylene glycol, propylene glycol, butylene glycol, triethylene glycol, 1,2,6-hexanetriol, thiodiglycol, hexyleneglycol, and diethylene glycol; glycerin; lower alkyl ethers of polyhydric alcohols such as ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, triethylene glycol monomethyl ether, triethylene glycol monoethyl ether, and triethylene glycol monobutyl ether; N-methyl-2-pyrrolidone, 2-pyrrolidone, 1,3-dimethyl-2-imidazoline, and the like. Among many aqueous organic solvents as listed above are preferred polyhydric alcohols, such as diethylene glycol, and lower alkyl ethers, such as triethylene glycol monomethyl ether.

Among these solvents, ethanol or isopropyl alcohol, or a lower alkyl ether of polyhydric alcohols is suitably used because its addition permits more stable bubble formation in ink on the thin-film resistor element in the discharging head in the case of a thermal jet printer.

In addition to the above-described components, the solution containing a cellular screening substance 12 can contain surfactants, antifoaming agents, preservatives, inorganic salts, organic salts, and others optionally, in order to prepare a solution with desired physical properties.

For example, surfactants can be any surfactant, as long as it dose not exert an adverse effect on cellular screening substances 12 in storage stability and others, and include, for example, anionic surfactants, such as fatty acid salts, higher alcohol sulfuric acid ester salts, liquid fatty oil sulfuric acid ester salts, and alkylallylsulphonate salts; and nonionic surfactants, such as polyoxyethylenealkyl ethers, polyoxyethylenealkyl esters, polyoxyethylenesorbitanalkyl esters, acetylene alcohol, and acetylene glycol. One or more surfactants of these can be selected and used as appropriate.

After cellular screening substances 12 are positioned to desired positions on a base 11 by micro-droplet discharging means 13, the substances 12 are immobilized on the base 11. In order to immobilize cellular screening substances 12 on a base 11, the cellular screening substances 12 or the base 11 may be subjected to pre-treatment necessary for immobilization. Treatments directed to the cellular screening substances 12 include: introduction of a functional group for covalent bonding such as amino, carboxyl, disulfide, epoxy, carbodiimide, and maleimido groups, or attachment of electrically chargeable materials for binding via electrostatic attraction force such as metals and inorganic oxide particulates, and cationic and anionic macromolecules. In order to achieve binding through biological affinity, on the other hand, avidin or biotin molecules, or materials capable of binding through biological affinity, such as antigen or antibody molecules can be attached to the substances. Alternatively, the surface of the base can be coated with a macromolecule or a silane coupling agent to introduce functional groups, such as amino, carboxyl, disulfide, epoxy, carbodiimide, and maleimide groups for covalent bonding, or in order to charge the base surface, a conductive or semiconductive layer can be formed in advance on the surface, for example, by using one of metals such as gold, silver, platinum, and iron, inorganic oxides such as indium tin oxide, titanium oxide, and zinc oxide, and furthermore conductive macromolecules such as polyacetylene, polypyrrole, polyaniline, and polythiophene, others. Otherwise, the surface of a base 11 can be provided with a substance that can bind to the bioaffinity substance introduced to the screening substance 12, which includes biotin or avidin, antibodies or antigens, and protein A having an antibody binding capability. Introduction of such a substance can strengthen binding force between the surface of a base 11 and cellular screening substances 12.

For immobilization, it is possible to apply energy externally by exposure to radiation including light, or by heating. Applying these external energies can promote the binding of the surface of a base 11 and cellular screening substances 12.

A cellular screening substratum 1 can be manufactured in the above-described procedure.

There will be now described a method of culturing cells on the cellular screening substratum 1 described above. By culturing cells on such a substratum, the cells will be cultured under the influence exerted on their adhesiveness, proliferation and differentiation, survival, maintenance of undifferentiated state, apoptosis, or production of substances. Cells are not limited specifically, and cells of any type can be used. One or more types of cells can be used for cellular screening. If necessary, sterilization treatment can be carried out by irradiating a cellular screening substratum 1 with ultraviolet light or the like, or by washing it with an alcohol solution before cell culture. These treatments allow preventing the culture from inhibition due to undesired microorganisms and the like. Although the culturing of cells can be performed by immersing the entire cellular screening substratum 1 into a culture medium, cells can be cultured under the influence exerted on their adhesiveness, proliferation and differentiation, survival, maintenance of undifferentiated state, apoptosis, and furthermore production of substances, so long as the region having the cellular screening substances immobilized therein is immersed in the culture medium.

Further, during culturing cells on the cellular screening substratum 1, or after culturing cells for a given period of time, it is possible to add a desired substance or substances to the culture medium for a desired region. This may result in alteration of cell proliferation and differentiation, survival, maintenance of undifferentiated state, apoptosis, or production of substances, and the adhesiveness to the substratum. It is also possible to add a desired substance or substances such as indicators to a desired region to facilitate screening after culturing cells.

During culturing cells on the cellular screening substratum 1, or after culturing cells for a given period of time, it is possible to remove a population of cultured cells from the substratum. When this is done, the substratum from which the cultured cells have been removed can be reused, and the removed population of cultured cells can be also used as artificially made living tissues or their portions. In specific procedures, a cellular screening substratum after culture can be trypsinized to remove a population of cultured cells, thereby reusing the substratum. This reuse of the substratum is one of the advantages provided by immobilizing cellular screening substances on the base, since cells cannot take in such cellular screening substances into the metabolite system. In addition, if a polymer such as poly(N-isopropylacrylamide) of which solubility in water varies with temperature is applied onto the substratum in advance, and after cell culture the temperature is reduced to about 30° C. or lower, the change of the hydration state on the polymer surface permits removal of a population of the cultured cells. Thus, the cell population can be utilized for living tissues and the like.

Next, there will be described a method of culturing cells on the above-described cellular screening substratum 1, thereby cellular screening and substances immobilized on the substance. As screening means can be utilized methods by which morphological changes in cells cultured on the above-described cellular screening substratum 1 are observed. One can employ any of microscopes, including optical microscopes, such as scanning electron microscopes, transmission electron microscopes, scanning probe microscopes, and fluorescence microscopes, as long as cell morphology can be observed. The cellular screening substratum on which cells have been cultured is placed at the observing position of the above-mentioned microscope, and cell morphology is observed with the microscope. Screening can be performed only by observing cell morphology under a microscope, and thus evaluation can be conducted by simple methods. Upon evaluation, the cells can be stained. Staining cells can facilitate evaluation with a microscope in the case where cells have been grown to high densities or fused to each other due to differentiation to form polykaryotic cells.

Besides morphological observation, one can utilize, as screening means, quantifying a substance produced by or incorporated into cells, during the course of or as results of the adhesion of cells to the substratum or the undergoing of proliferation and differentiation of cells. If a subject to be quantified is not measurable directly, an alternative substance can be quantified. Specifically, genetic engineering can be used to integrate a gene of a quantitatively measurable protein in the vicinity of the gene of a desired subject protein to be quantified, so that the desired protein can be quantitatively determined by quantifying the quantitatively measurable protein. By determining these substances, it is possible to investigate in detail what intracellular changes are caused by the substances immobilized on the substratum, leading to the elucidation of signal transduction mechanisms within the cells. In the case where evaluation is conducted with a substance incorporated into the cells, a measurable indicator can be provided in advance to a substance which will be incorporated, allowing quantification with relative ease.

Quantifying of these substances involves methods of measuring the amount of radiation emitted from a radioactive compound, methods of measuring the amount of fluorescence emitted from a substance labeled with a fluorescent substance, and furthermore methods of measuring the amount of light emitted from a light-emitting substances, and methods of measuring the absorbance of a dye.

In methods of measuring the amount of radiation emitted from a radioactive compound, a method employing a compound substituted with a radioisotope element abundant in the body, such as hydrogen, carbon, nitrogen, phosphorus, and sulfur, to measure the radiation emitted from the compound is highly sensitive. In addition, since such a compound has the same chemical properties as those of cold compound, activities of the cellular metabolism is not affected, thus permitting observation of similar phenomena to those within the living body.

Labeling with a fluorescent substance is relatively easy, and since such fluorescent substances are low molecular weight compounds, they will exert a slight effect on activities of the cellular metabolism. In addition, when a substance produced by the cells is quantified by quantitative methods using an antigen-antibody reaction, various antibodies labeled with fluorescent substances are commercially available and have high sensitivities for measurement. Thus, evaluation with fluorescent measurements is effective.

In methods of measuring the amount of light emitted from a light-emitting substance, it is possible to measure the emitted light amount at high sensitivities, so that significantly small changes can de detected. In the case where a gene has been identified which is expressed accompanying with adhesion, proliferation, differentiation, or production of substance caused by the cellular screening substances, a firefly luciferase gene or the like can be introduce near that gene, and amounts of the luciferase produced in conjunction with the gene expression can be measured by means of the amount of light yielded by addition of ATP and luciferin. In this way, the effects caused by the screening substances can be evaluated by virtue of the amount of light emission.

In methods of measuring the absorbance of a dye, it is possible to amplify the absorbance of a dye, in combination with enzyme reactions and the like, thereby measuring quantitatively a substance occurring in very small amounts.

The following describes an apparatus for culturing cells on the above-described cellular screening substratum and for screening cells and substances immobilized on the substratum. This aspect of the present invention is characterized by positioning and immobilizing two or more cellular screening substances in desired areas on a base by micro-droplet discharging means, and culturing cells in a culture medium in contact with the areas of the immobilized cellular screening substances on the cellular screening substratum having plural areas of different functions, and furthermore it can involve means of manufacturing the above-described cellular screening substratum, or at least one of means for evaluating changes in cell morphology cultured by the culturing means, means for measuring quantitatively a substance synthesized within the cells, and means for measuring quantitatively a substance incorporated into the cells.

Figure 6:
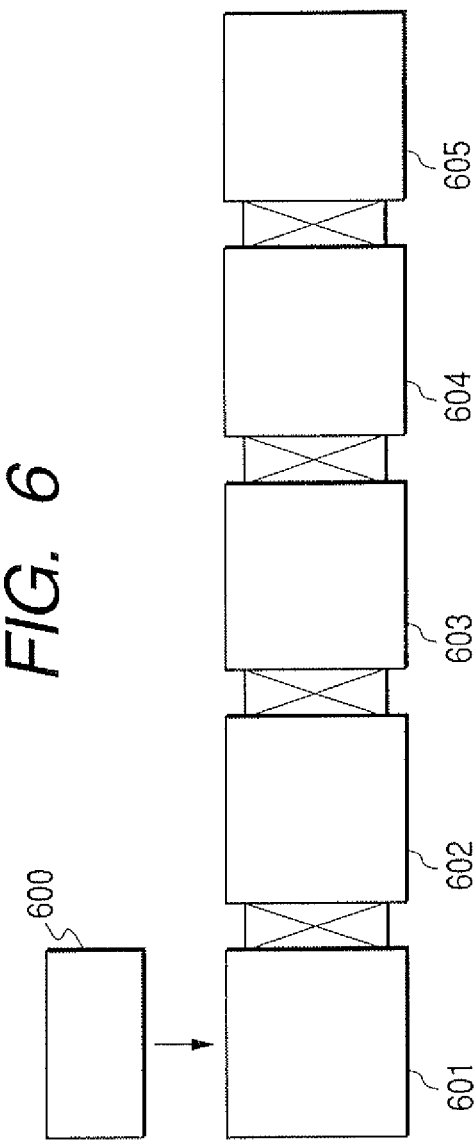
FIG. 6 shows a block diagram of the apparatus for cellular screening according to the claimed invention.

FIG. 6 shows a block diagram of the apparatus according to the claimed invention. A base (600) is supplied from the base supplying chamber (601) of the apparatus. In the screening-substance applying chamber (602), screening substances are applied on the base with micro-droplet discharging means, and then in the immobilizing chamber (603), immobilized by exposing it to light or heat to manufacture a cellular screening substratum. Next, the resulting substratum is transferred into the culturing chamber (604) and cells are cultured on the substratum by the above-described method, followed by cellular screening in the detection chamber (605), by observing morphological changes of cells, cell adhesiveness, proliferation and differentiation, survival, maintenance of undifferentiated state, apoptosis, or production of substances, or by the above-described quantifying means.

Figure 7:
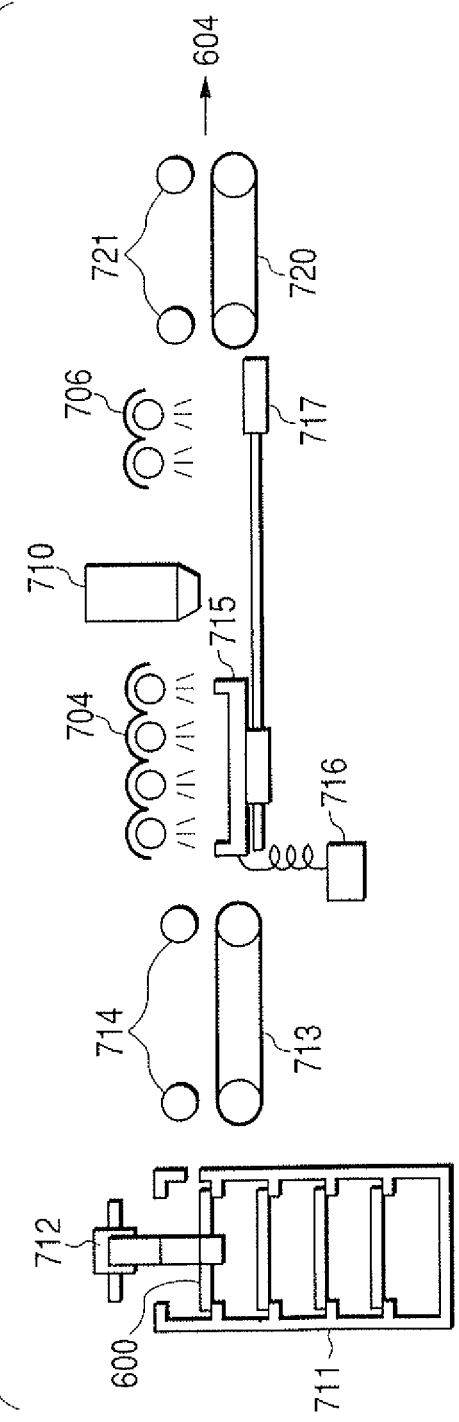
FIG. 7 shows an illustration of means for manufacturing a cellular screening substratum of the apparatus for cellular screening according to the claimed invention.

Chambers 601 to 603 can be represented, for example, by apparatus as shown in FIG. 7, wherein 710 designates a micro-droplet discharging apparatus. Substrata 600 are set in the stocker 711, and a substratum is transferred to the belt conveyor 713 through the transferring machine 712 and sent to the tray 715. 714 designate sending auxiliary rollers. The substratum 600 sent into the tray 715 is attracted and immobilized tightly onto the tray by the suction of the pump 716. The substratum 600 on the tray 715 is sent into an area where a first treatment step is carried out. Numeral 704 designates a UV/$O_3$ lump which provides the pre-treatment of the base. When the base is transferred out of the first step area by the sending motor 717, cellular screening substances are applied with the micro-droplet discharging means 710. The base on which the cellular screening substances have been applied is transferred immediately to an area where the third immobilizing-treatment step is carried out, and the cellular screening substances are immobilized on the base. Numeral 705 designates a UV irradiating lump. The base which has undergone these three treating steps is transferred to the subsequent step 604 via the belt conveyor 720 and sending rollers 721.

However, the cellular screening apparatus according to the claimed invention are not limited to these embodiments, if the foregoing purposes are achieved, even though they are different from these embodiments.

When it is not known what substance or which combination of substances affect cellular functions of a certain cell type, at least one function selected from the group consisting of adhesion, proliferation, differentiation, survival, maintenance of undifferentiated state and substance production, the cellular screening substratum of the present invention can be used to investigate such substances or combinations. Once such a substance or substance combination was elucidated as a result of the investigation, cells can be screened by using another cellular screening substratum that is produced by disposing or disposing and immobilizing such a substance or substances, or combinations on a base by using, for example, microdroplet ejection means to screen cells. Further, when a plurality of substances or combinations, each of which affects different cellular function, are arranged or immobilized after arrangement, one can obtain a cellular screening substratum that enables screening of plural types of cells at the same time.

EXAMPLES

The present invention is described in more detail by Examples. These Examples are specific embodiments presented to provide better understanding of the present invention, and not intended to limit the present invention thereto in any way.

Example 1

Cellular Screening Method of Evaluating Cell Growth Factors

A functional group was introduced in the following way, in order to immobilize cellular screening substances on a base. A solution of 50 mmol dicyclohexylcarbodiimide (DCC) in tetrahydrofuran (THF) was added dropwise to a solution of 50 mmol N-hydroxysuccinimide and 45 mmol 4-azidobenzenecarboxylic acid in THF, and the reaction was carried out reacted at 4° C. for 24 hours with stirring. The reaction product was dried under reduced pressure, and then recrystallized and purified from an isopropanol/diisopropanol solution. Subsequently, the reaction product was dissolved in dimethylformamide, and to this solution was added in small portions cellular screening substances dissolved in an isotonic phosphate buffer solution (pH 7.0). The reaction was carried out at 4° C. for 48 hours to introduce azido groups into the cellular screening substances.

In this Example, as the cellular screening substances were used insulin, basic fibroblast growth factor (basic FGF), epidermal growth factor (EGF), transforming growth factor-beta (TGF-●), and azide groups were introduced to each of these factors. Ink cartridges were washed with purified water, and then filled with isotonic phosphate buffer solutions (pH 7.0) containing each of the cellular screening substances having the introduced functional group and which were diluted in 50% methanol solution to a concentration of 50·g/ml.

Next, as shown in FIG. 1, each of the cellular screening substances 12 was discharged on a base 11 of a polyethylene terephthalate (PET) film with an ink jet printer. Each cellular screening substances 12 was discharged to respective areas for immobilizing insulin 121, basic fibroblast growth factor 122, epidermal growth factor 123, and transforming growth factor-● 124, such that the substances were not overlapped to each other. After drying droplets, a UV lump was used to irradiate the surface of the base 11 with UV light to immobilize the cellular screening substances 12. The base 11 was then washed with an isotonic phosphate buffer solution (pH 7.0) to remove unreacted cellular screening substances 12. A cellular screening substratum 1 was manufactured in these procedures.

Cellular screening was carried out on this cellular screening substratum 1.

The screening substratum which had been sterilized in advance under a sterilizing lump was placed into a glass petri dish, and as the culture medium was used a DMEM medium (Dulbecco's Modified Eagle's minimum essential medium) supplemented with 10·g/ml transferin. On the screening substratum, vascular endothelial cells were cultured under humidified air containing 5% $CO_2$ at 37° C. for 24 hours. The culture medium also contained $^3$H-thimidine, and the amount of $^3$H-thimidine incorporated into the cells by growth was determined from the amount of $^3$H radiation in order to assess the degree of proliferation.

When the substratum after culture was observed under a microscope, growth of cells was observed in the insulin, basic-FGF, and EGF immobilized areas, but not in the TGF-● immobilized area.

The growth density of cells was determined from the amount of $^3$H radiation. The insulin-immobilized area had a growth density of 10000 cells/mm$^2$, the basic-FGF immobilized area of 6000 cells/mm$^2$, the EGF immobilized area of 8000 cells/mm$^2$, and the TGF-● immobilized area of 100 cells/mm$^2$. These results demonstrated that insulin, basic-FGF, and EGF have a growth activating effect on vascular endothelial cells, whereas TGF-● does not have such an effect.

Example 2

Cellular Screening Method of Evaluating Cell Growth/Differentiation Factors

Figure 3:
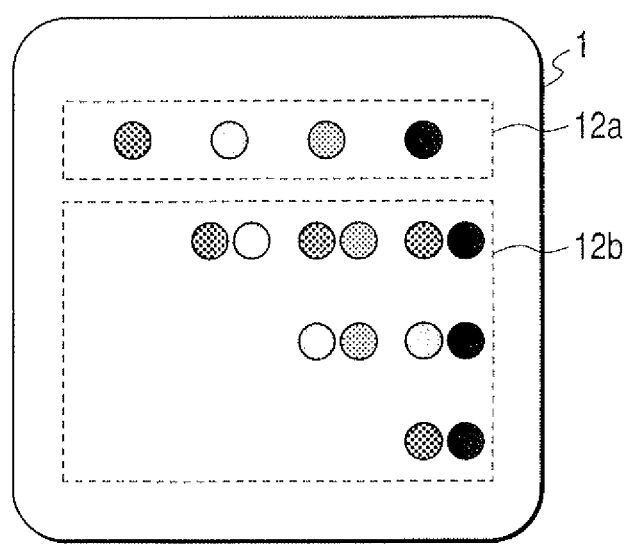
FIG. 3 is an example of positioning cellular screening substances on the cellular screening substratum of Example 2.

Azide groups were introduced into insulin-like growth factor-1 (IGF-1), basic-FGF, EGF, and TGF-● by the above-described method for introducing an immobilizing functional group. As in Example 1, an ink jet printer was used to discharge individual cellular screening substrata on a PET film to immobilize them on a base. In this Example, the array or pattern was as shown in FIG. 3. As shown in FIG. 3, on the substratum were provided an isolated immobilized area 12*a* in which each of four cellular screening substances was immobilized separately, and an interactive immobilized area 12*b* in which two of the cellular screening substances were close immobilized. Like this, one of the major advantages of using droplet discharging means for applying cellular screening substances to a base is that plural areas can be easily formed on the same base varying the positional relationship between the immobilization positions of two or more cellular screening substances.

Chicken skeletal muscle cells were cultured on this substratum using a DMEM medium supplemented with 10·g/ml fibronectin, under similar conditions to those in Example 1. The state of proliferation and differentiation was evaluated using an Amersham Cell proliferation kit. This kit is for determining the amount of synthesized DNA by a fluorescence antibody method using a fluorescein-isothiocyanate (FITC) labeled antibody to 5-bromo-2'-deoxyuridine (BrdU). In addition, the growth density was determined by staining the cells after culture. This procedure involved treating the cultured cells with methanol for 30 minutes, followed by drying them and staining the nuclei by an 10000 fold dilution of Hoechst 33258 for 5 minutes. Excess staining solution was washed away with an isotonic phosphate buffer solution. The substratum was placed on a glass slide, and covered with a cover glass after dropping glycerin. The substratum was observed under a fluorescent microscope to count the number of stained nuclei. The number of nuclei containing DNA labeled with BrdU was determined quantitatively by a fluorescence quantification method. As a consequent, in IGF-1 and EGF areas increased fluorescence and close-packed nuclei were observed. It can be understood from these results that the proliferation and differentiation of the cells were promoted. In basic-FGF area, fluorescence increased but the cell nuclei were dispersed, indicating that the proliferation was activated, but the differentiation was not promoted. In TGF-● area, the increase in fluorescence was not substantial, so that it is considered that the proliferation was not promoted. In the area 12*b* where combinations of two cellular screening substances were arranged, it was observed that with the combination of IGF-1 and EGF, each of which was active in proliferation and differentiation in the area 12*a*, cell proliferation was suppressed with no increase in the fluorescence amount. From these results, it has been found that a combination of cellular screening substances that are active singly may exert a suppressive effect.

Example 3

Allergen Screening Method

In this Example, constitution of a subject is evaluated whether it is allergic or not by using a substratum with immobilized possible allergenic substances and cells taken from the subject and determining the amount of histamine, inflammation causing substances produced by the cells during culture.

Figure 4:
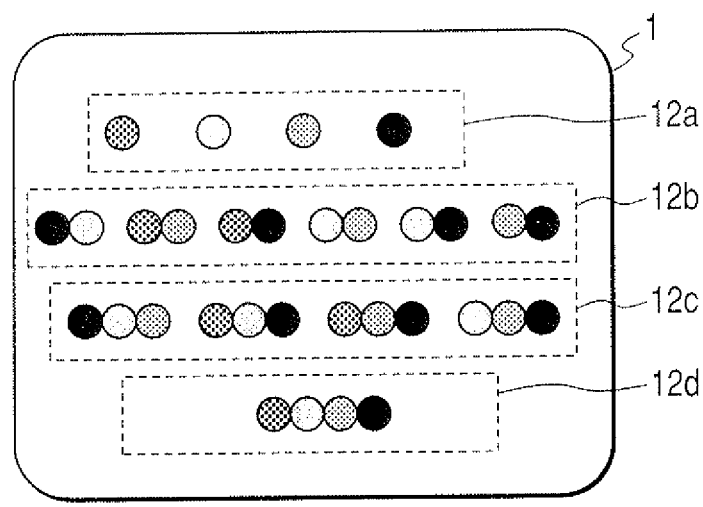
FIG. 4 is an example of positioning allergens on the allergen screening substratum of Example 3.

In this Example, a substratum as shown in FIG. 4 was manufactured for assessing whether a subject is allergic to cedar pollens, milk, house dusts, or wheat. The substratum was provided with, in addition to an area 12a in which allergens were immobilized singly, a two-substance immobilized area 12b, a three-substance immobilized area 12c, and four-substance immobilized area 12d in which two, three, and four allergens were close immobilized respectively, so as to diagnose whether allergy may be caused by the synergetic effect of two or more allergens.

Cedar pollens, house dusts and wheat were fully grinded by a homogenizer, and solutions containing each allergen were centrifuged, and the solubilized fractions other than precipitation were used for immobilization. Each allergen solution was then diluted in 50% methanol to a concentration of 50·g/ml and immobilized on a PET film with an ink jet printer by the method described in Example 1. The immobilization pattern was as shown in FIG. 4. The area not subjected to immobilization was coated with bovine serum albumin to prevent non-specific adsorption.

Cells were collected from the blood of a subject to be assessed, and blood components were separated by a density gradient centrifugation to collect allergy-reactive cells.

The culture medium was a DMEM medium containing 10% fetal bovine serum (FBS). An anti-histamine antibody (rabbit) was added and the cells were cultured on the substratum.

The substratum was removed after culture and washed with an isotonic phosphate buffer solution. After treating the substratum with methanol for 30 minutes and drying, the histamine amount was determined by an enzyme antibody method using a horseradish peroxidase-conjugated anti-rabbit IgG antibody, measuring changes in the absorbance of o-phenylenediamine. As a result, a high amount of histamine was detected in the area where the extract of house dusts was immobilized, therefore it is likely that this subject is allergic to house dusts. Although this subject is considered negative to the cedar pollens, milk, and wheat, it was found that a high amount of histamine was detected in the area where milk and wheat were immobilized in close vicinity, so that the subject may develop allergy when both allergens are taken at the same time.

As described above, use of the substratum of the invention enables determining the cause of allergy. In particular, it enables diagnosis of an allergic reaction directed to plural allergens, as in this Example.

Example 4

Figure 5:
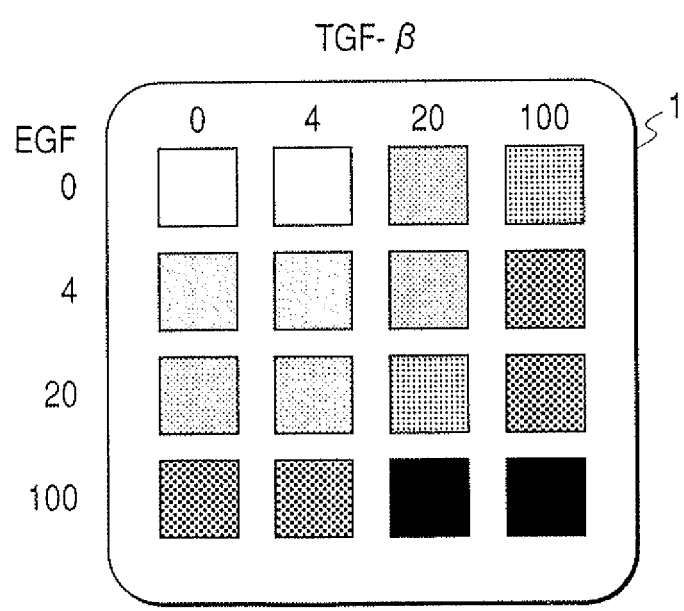
FIG. 5 is an example of positioning cellular screening substances on the screening substratum of Example 4.

Proliferation/Differentiation Screening Method with Different Densities of Immobilized Substance In this Example, effects of EGF and TGF-● on cell growth of fibroblast NRK cells were studied. Azide groups were introduced into these two cell growth factors EGF and TGF-● in advance according to the Example 1. The base was a PET film, and an ink jet printer was used to discharged cell growth factors respectively onto the substratum to dispose the factors varying the density according to the positions on the base as shown in FIG. 5. After drying, the base was irradiated with ultraviolet light to immobilize the cell growth factors. The discharge amount was controlled by setting the dot density of drawing data for respective areas, which data were sent from the computer to the printer. The figures indicated in FIG. 5 are relative dot densities of each growth factor in a row or column direction, and each area where a row and a column of respective densities cross, two growth factors are immobilized at respective dot densities.

NRK cells were cultured on the substratum thus manufactured. The culture medium was a DMEM medium supplemented with BrdU and 0.5 wt % FBS, and culture was carried out under humidified air with 5% $CO_2$ at 37° C. for 48 hours.

After culture, evaluation was made using an Amersham Cell proliferation kit. The results are shown in Table 1.

TABLE 1

| Cell Density | | TGF-● Density | | | |
|---|---|---|---|---|---|
| $10^5$ cells/mm² | | 0 | 4 | 20 | 100 |
| EGF | 0 | 14 | 42 | 34 | 30 |
| Density | 4 | 40 | 14 | 13 | 14 |
| | 20 | 60 | 12 | 12 | 10 |
| | 100 | 80 | 20 | 20 | 20 |

It is considered that the growth of NRK cells is promoted by single EGF or TGF-● but suppressed by combinations thereof. From these effects of EGF and TGF-● on cell growth of the NRK cells, it is desirable to culture NRK cells in a culture medium containing either of EGF and TGF-● not both.

The cellular screening substrata of the present invention have advantages that cellular screening substances can be immobilized at desired positions by simple processing steps and identifying substances contributing to at least one of adhesion, proliferation and differentiation, survival, maintenance of undifferentiated state, and apoptosis.

The methods of cellular screening of the present invention make it possible to investigate effects on a cell exerted by various substances on a single substratum, and additionally the difference of the effects on different cells exerted by various substances.

What is claimed is:

1. A process for manufacturing a cellular screening substratum, comprising steps of:
    ejecting a first solution containing a first substance and a second solution containing a second substance from an inkjet head as micro-droplet discharging means onto a base so as to form a plurality of areas where the first and second substances are positioned with different densities, the first and second substances being different cellular screening substances selected from extracellular matrix proteins, antibodies and cytokines and having a reacting group for binding to the base; and
    immobilizing the first and second substances onto the base, each via the reacting group, by applying energy selected from the group consisting of radiation and heating to the base after the ejection.

2. The process for manufacturing a cellular screening substratum according to claim 1, wherein the micro-droplet discharging means is a thermal inkjet.

3. The process for manufacturing a cellular screening substratum according to claim 1, wherein the micro-droplet discharging means is a piezoelectric inkjet.

4. The process for manufacturing a cellular screening substratum according to claim 1, wherein the substratum is flat.

5. A process according to claim 1, wherein the first and second solutions are ejected respectively as liquid droplets each having a volume of 100 pL or less per droplet.

6. The process according to claim 1, wherein a third solution containing a third substance which is not the same as either one of the first and second substances is further ejected in the ejecting step, and the third substance is immobilized onto the base in the immobilizing step.

7. The process according to claim 6, wherein a fourth solution containing a fourth substance which is not the same as any one of the first to third substances is further ejected in the ejecting step, and the fourth substance is immobilized onto the base in the immobilizing step.

8. A cellular screening substratum manufactured by the process for manufacturing a cellular screening substratum according to claim 1.

9. The cellular screening substratum according to claim 8, wherein at least one of the first and second substances is a cytokine.

10. The cellular screening substratum according to claim 9, wherein the cytokine is a growth factor or a hormone.

11. The cellular screening substratum according to claim 10, wherein the growth factor is a nerve growth factor, an epidermal growth factor, or a fibroblast growth factor.

12. The cellular screening substratum according to claim 10, wherein the hormone is insulin or adrenaline.

13. A method for cellular screening using a cellular screening substratum according to claim 8, comprising:
    culturing the cells in a culture medium in contact with predetermined areas on the base.

14. The method for cellular screening according to claim 13, comprising:
    adding a substance used to screen the cells to the culture medium in contact with the predetermined areas.

15. The method for cellular screening according to claim 13, wherein the predetermined areas are in contact with a flow of the culture medium.

16. The method for cellular screening according to claim 13, further comprising:
    observing morphological change of the cells.

17. The method for cellular screening according to claim 16, wherein the cells are stained upon evaluation.

18. The method for cellular screening according to claim 13, comprising:
    measuring quantitatively a substance which has been synthesized within the cells.

19. The method for cellular screening according to claim 13, comprising:
    measuring quantitatively a substance which has been incorporated into the cells.

20. The method for cellular screening according to claim 18, comprising:
    measuring quantitatively the substance which has been synthesized within the cells by determining the amount of radiation, fluorescence, light emission or absorbance.

21. The method for cellular screening according to claim 19, comprising:
    measuring quantitatively the substance which has been incorporated into the cells by determining the amount of radiation, fluorescence, light emission or absorbance.

22. An apparatus for cellular screening comprising:
    a cellular screening substratum according to claim 8; and
    a culturing chamber constructed to culture the cells in a culture medium in contact with predetermined areas on the base.

23. The apparatus for cellular screening according to claim 22, wherein the apparatus further comprises at least one of means for observing morphological changes of the cells, means for measuring quantitatively a substance which has been synthesized within the cells, and means for measuring quantitatively a substance which has been incorporated into the cells by the culturing chamber.

24. The apparatus for cellular screening according to claim 22, wherein the apparatus further comprises means for manufacturing the cellular screening substratum.

* * * * *